United States Patent [19]

Aldridge et al.

[11] 4,146,018
[45] Mar. 27, 1979

[54] FLUID PRESSURE MEASURING OR TESTING SYSTEM AND BLEED REGULATION THEREOF ACCORDING TO SCHEDULE

[75] Inventors: Clarence F. Aldridge, Asheville; Donald H. Peeler, Hendersonville, both of N.C.

[73] Assignee: Sybron Corporation, Rochester, N.Y.

[21] Appl. No.: 764,342

[22] Filed: Jan. 31, 1977

[51] Int. Cl.² ............................................. A61B 5/02
[52] U.S. Cl. .................. 128/2.05 G; 73/748; 251/7; 251/297
[58] Field of Search .............. 128/2.05 G, 2.05 A, 128/2.05 C, 2.05 M, 274, DIG. 28, 210, 211; 251/7, 297; 138/46; 73/402, 748

[56] References Cited

U.S. PATENT DOCUMENTS

| 1,238,521 | 8/1917 | Janish, Jr. .................... 251/7 |
| 3,198,194 | 8/1965 | Wilburn ................ 128/DIG. 28 |
| 3,504,663 | 4/1970 | Edwards ................. 128/2.05 G |
| 3,779,236 | 12/1973 | Stewart ................... 128/2.05 G |
| 4,050,311 | 9/1977 | Leach ..................... 128/2.05 G |

FOREIGN PATENT DOCUMENTS

| 334539 | 1903 | France ......................... 251/7 |
| 1317101 | 12/1962 | France ......................... 251/7 |

*Primary Examiner*—Lee S. Cohen
*Attorney, Agent, or Firm*—Theodore B. Roessel; Joseph C. MacKenzie

[57] ABSTRACT

A sphygmomanometer system having a cuff, etc., and including both a regulator valve which normally bleeds the cuff pressure down at a substantially constant slow rate, and an exhaust valve which is operable to provide three rates of bleed, to wit nil, fast (as compared to the regulator valve bleed rate) and dump, the two valves together providing cuff bleed in accordance with predetermined schedule. The exhaust valve includes an elastic annular member compressible to achieve the fast and dump rates.

8 Claims, 4 Drawing Figures

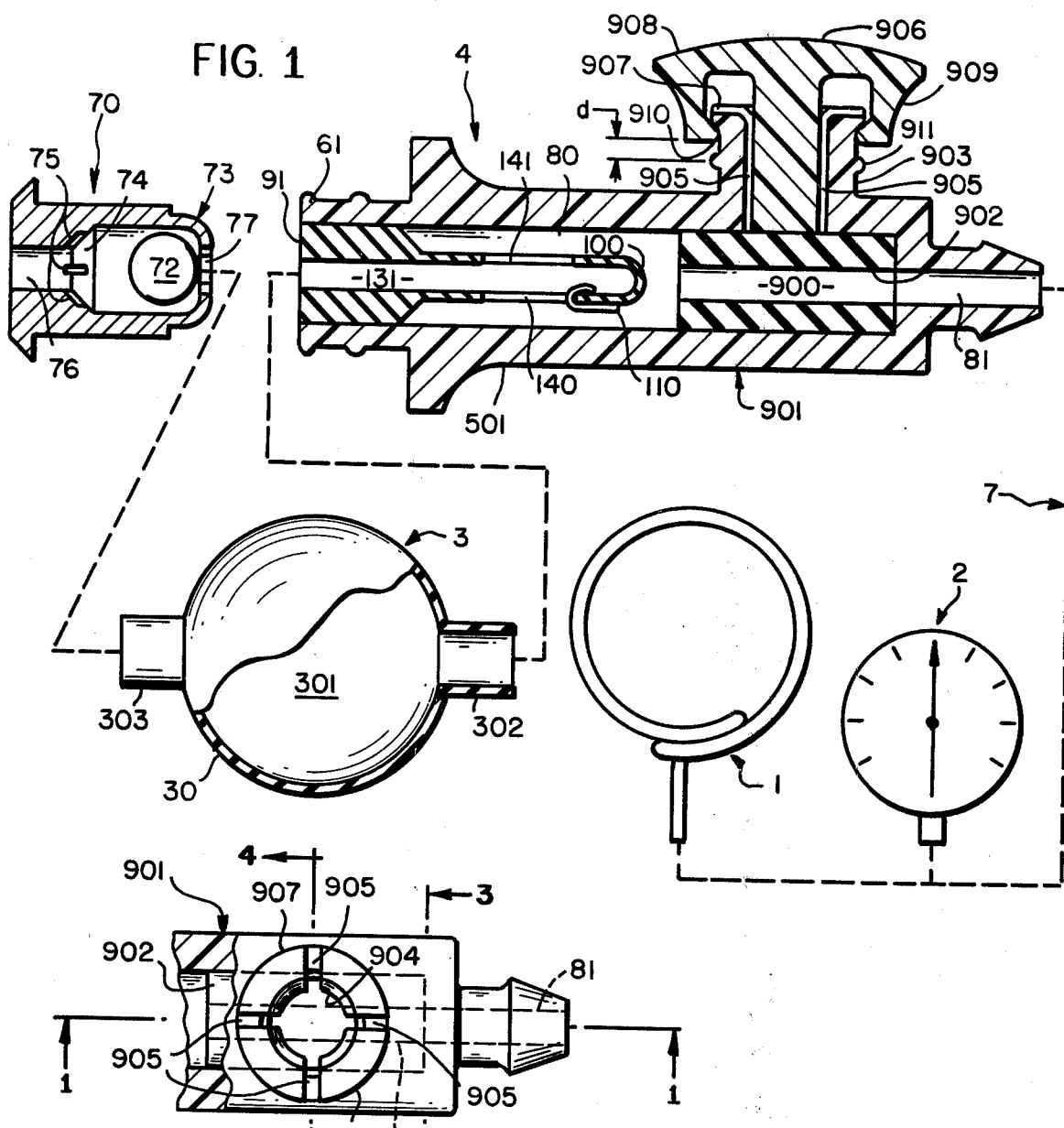
FIG. 1
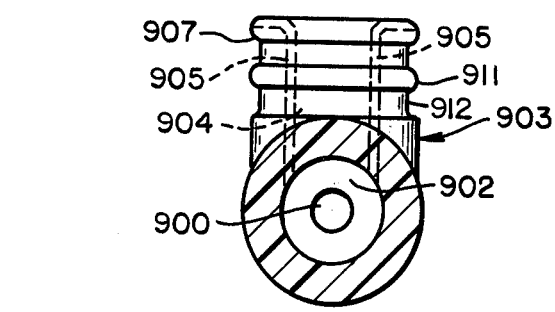
FIG. 2
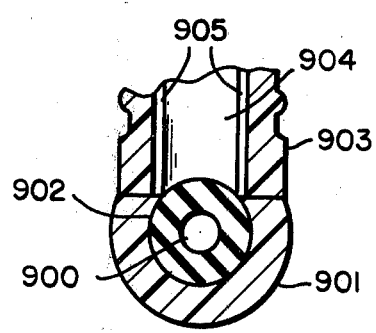
FIG. 3
FIG. 4

FLUID PRESSURE MEASURING OR TESTING SYSTEM AND BLEED REGULATION THEREOF ACCORDING TO SCHEDULE

RELATED APPLICATIONS

The two sole applications of Donald H. Peeler, Ser. No. 764,340 and Ser. No. 764,341 filed on the same day, assigned to the assignee of the present application, entitled Fluid Pressure Measuring Or Testing Systems And Bleed Regulator Valve Therefore, the detailed descriptions of which are to be considered as part of the detailed description of the present invention.

FIELD OF THE INVENTION

The present invention relates to measuring and testing by applying fluid pressure in a plenum physically related to the test subject or object and allowing the pressure to bleed down at a predetermined rate. In particular, our invention relates to sphygmomanometry wherein the plenum is a cuff arranged on a living being for occluding an artery of such being. A pump is provided to pump the cuff up, after which the air is released while Korotkow sounds, cuff pressures, and/or the like are monitored.

DESCRIPTION OF THE PRIOR ART

The above-identified Peeler sole applications describe and claim sphygmomanometer systems and regulator valves wherein cuff bleed is managed according to various expedients. The particular object of the present invention is to provide an improved exhaust valve providing cuff pressure bleed rates which are both well-controlled and easy to control manually. The present invention otherwise has substantially the same objects as the invention described in the Peeler applications.

SUMMARY OF THE PRESENT INVENTION

In the present invention, a housing incorporating a regulator valve, also incorporates a normally closed exhaust valve, which is manually operable to provide fast bleed and dump states. The valve is operated by a plunger, which when pushed a certain distance, unseats a valve element, and thereby creates a restricted bleed path previously sealed by the valve element. Pushed further, the plunger in effect clears the bleed path and dumps the cuff through the now-constricted, now-unconstricted bleed path.

The normally closed exhaust valve has a valve element in the form of a compressible annular member or sleeve concentric with the main chamber in the housing of the regulator valve. The bleed path goes out through the side of the housing between the ends of the sleeve, and includes the interface between the sleeve exterior and the interior surface of the main chamber. In the bleed path is located the plunger, which would restrict the path but is bypassed by channels so that only the sleeve can provide a bleed-restricted effect on the bleed path.

BRIEF DESCRIPTION OF THE DRAWING

FIG. 1 shows a sphygmomanometer system according to the invention, which incorporates an exhaust valve according to the invention.

FIGS. 2, 3 and 4 are views of details of the exhaust valve according to the invention.

DESCRIPTION OF THE PREFERRED EMBODIMENTS

Except for the details of the exhaust valve, and its contribution to the system operation, the system of FIG. 1 is effectively and amply described by Peeler's sole applications, above-identified, hence insofar as appropriate, the same reference numerals will be used herein to indicate elements in common.

Thus, the system comprises cuff 1, pressure gauge 2, pump 3, and regulator valve 4. The valve 4 has a nipple 100, slits 140 and 141, and variable opening (not shown here) created by "d"-shaped member 110 passing through one end of slit 140, and nipple 100 terminates in an integral annular base 91. Regulator valve 4 has housing 501 which has a fitting 903, which includes exhaust valve structure to be described infra.

Pump 3 has a rubber or other elastomer bulb 30 hermetically fitted by an integral collar 302 over fitting 61 of regulator valve 4. Another integral collar 303 provides for receiving a check valve 70. Check valve 70 has the usual function of allowing air to be drawn into the interior volume 301 of bulb 30, when the bulb, after having been squeezed, is released and, to a degree, also has the usual function of preventing the air in interior volume 301 from being expelled to the atmosphere surrounding bulb 30, when the bulb is squeezed. However, the check valve, which has the general form of the usual fitting having ball 72, cage 73, and conical seat 74, also has grooves 75 in the seat 74, so that when the ball is in the seat, grooves 75 prevent it from sealing off volume 301 from the external atmosphere. The atmosphere otherwise has access to volume 301 through fitting 70, via bore 76 into cage 73, around ball 72 which fits cage 73 sufficiently loosely as not impede air flow between it and the cage structure, which has opening 77 the form of which keeps the ball from sealingly seating therein at any time, but instead always will allow free flow of air therethrough, whether it be to or from interior volume 301.

Air can be forced, from inside nipple 100, out through slits 140 and 141, relatively freely, whereas air can be forced into the nipple 100 only restrictedly, because positive pressure, acting on the outside of the nipple, tries to hold the slits closed, except for the slight opening (not shown) created by member 110.

When the plenum formed by cuff 4, gauge 2, tubing 7, and chamber 80 contains a gas under pressure higher than that of the atmosphere surrounding such plenum, the gas will leak out of the plenum through regulator valve 4, provided pump 3 allows it, which in fact is the reason for providing a leaky check valve 70. Mor particularly, the flow resistance of the check valve, from volume 301 to atmosphere, with ball 72 seated and thereby allowing air plow solely through grooves 75, is chose to be less than would allow the pressure in volume 301 to build up enough above atmosphere pressure such as would prevent regulator 4 from regulating flow into chamber 80, from cuff 1, such that the pressure in cuff 1 bleeds down at a constant rate to the minimum useful or desired cuff pressure, for example, a value below the minimum expected diastolic pressure value, e.g., less than 40 mm. Hg gauge, say about 25 mm. Hg gauge.

Conversely, one expects to inflate the plenum to some super-atmospheric pressure, as in the case of cuff 1, where one would like to get the pressure to 300 mm. Hg gauge, before bleeding down. Accordingly, when one squeezes the bulb, the grooves 75 have to restrict flow to atmosphere enough to allow the pressure in volum 301 to get up to 300 mm Hg (the nipple 100 will be flexible enough that there is substantially nil resistance to air flow from inside the nipple out through the slits 140 and 141), so that the cuff can be pumped up to substantially the highest pressure that can be generated by compressing the bulb 30 in the presence of leakage through the check valve 70.

The main chamber 80 of regulator valve 4 extends into an exhaust valve housing portion 901 of regulator valve housing 501, portion 901 containing an annular elastic member or sleeve 902 having a bore 900 which is more or less an extension of the bore 81, via which the valve 4 communicates with inflatable cuff 1 and manometer 2.

As the FIGS. indicate, the sleeve 902 is right circularly cylindrical in shape, as is the chamber 80 (or at least that portion thereof in the exhaust valve housing portion 901 which contains sleeve 902). As sleeve 902 is to provide a valve member, its external surface and the corresponding inner surface of chamber 80 are smoothly finished, and the outer diameter of the sleeve is large enough so that the sleeve has an interference fit in chamber 80, such fit being tight enough to create a fluid seal at the interface between the sleeve surface and the chamber surface. Harking back to the intended operation of the system, the just-described state of sleeve 902 corresponds to the slow bleed of cuff pressure through regulator valve 4 which is desired while the system is in the vicinity of diastole or systole.

As pointed out by Peeler, however, it is desirable to have a fast bleed available in order to get to such "vicinity" quickly and to be able to dump the cuff after diastolic pressure has been measured.

For such purpose, housing portion 901 is provided with a fitting 903 having a central bore 904, in the sides of which are channels 905, (four, say, 90° apart, as shown in FIG. 2), and receiving a plunger 906. The channels extend to, and open in, chamber 80, and also to and across the outer end face of fitting 903 and through the generally right circularly cylindrical exterior surface of the fitting at the flanged portion 907.

The plunger 906 serves to compress sleeve 902, being provided for that purpose with a thumb-pressable cap 908 having a skirt 909 terminating in an inwardly directed circular flange 910. The flange 910 is lesser in diameter than flange 907 and is elastic, so it can be forced over the flange 907 into the annular space between flange 907 and a circular flange 911 intermediate the ends of the fitting 903, in order to secure it in place yet permit vertical motion of the plunger 906 at least to the extent of the spacing between flanges 907 and 911.

Preferably the plunger 906, cap 908, flange skirt 909 and flange 910 are made from a single piece of rather stiff plastic, whereas the sleeve 902 is made from a single piece of rather flexible rubber, or the like. This allows the plunger to be pressed downward by the thumb such as to compress the sleeve 902 without appreciably deforming the plunger. At the same time, skirt 909 will have enough resilience that the plunger and cap can be assembled to the fitting 903 in the first place.

The number and dimensions of channels 905 are chosen to allow free air flow therethrough collectively, whereas the dimensions of plunger 906 are chosen to otherwise substantially exactly fill bore 904, but not fitting so tightly therein to prevent sleeve 902's resilience from normally sealing (when the plunger is released) the lower openings of bore 904 and channels 905.

The distance d, FIG. 1, represents how far the plunger 906 can move downward before further motion is palpably resisted by flange 911, and is calculated to create enough space in the interface between sleeve 902 and chamber 80 that a fast cuff bleed obtains. Thus, as disclosed in Peeler, after the cuff has been pumped up to a pressure greater than systolic, one may not want to wait out the regulator valve's slow bleeding of the cuff. With our novel exhaust valve, the thumb is used to push plunger 906 in as far as is necessary to increase the bleed to the desired rate, a point at which the plunger is held for as long as need be. At this point, the slow bleed function of the regulator valve becomes of no moment, of course, unless the plunger is released, in which case the sleeve 902 will once again seal bore 902 and channels 905.

As indicated in FIG. 3, there is an additional annular space 912, similar to that between flanges 907 and 911. Plunger 906 can be pushed down by the thumb far enough to snap the flange 910 over the flange 911, and also far enough to compress sleeve 902 so much that the space between its peripheral surface and the inner surface of chamber 80 is large enough that the air in cuff 1 has substantially unimpeded access via such space, to channel 905. This results both in dumping the cuff pressure to the ambient atmosphere and in locking the plunger 906 in place. This allows the user to let go the valve and attend to other matters such as unfastening and removing the cuff and squeezing the last air out of it, in preparation for the next application thereof (before which the plunger will have to be pulled up by hand in order to allow the cuff to be pumped up again.)

Suitable precautions need be taken to assume that air flow to ambient atmosphere from channels 905 is not impeded by the skirt 908, flanges etc. This can be achieved by suitable dimensioning of the cap 908 and fitting 903, and in any event could also be assured by simple expedients such as vent through suitable channels (not shown) and/or holes (not shown) in skirt 909, the flanges and so on, as will be obvious to those skilled in the art.

As will be seen from the foregoing, the novel exhaust valve and the Peeler regulator together provide a cuff bleed rate schedule having three stages; one a fixed slow rate of pressure bleed due solely to regulator valve 4, because the exhaust valve itself is providing pressure bleed at a nil rate, so to speak. The second is a fast rate of bleed (and variable, within the limits of FIG. 1, to suit the user), and the third is a dump rate. The bleed rate program is powered by the thumb, so to speak, in an entirely uncomplicated way, which creates no distractions, since no appreciable amount of adjusting motion has to be undertaken, especially as compared to fiddling with prior art thumb-screw operated bleed valves.

Having described our invention, we claim:

1. A sphygmomanometric system comprising fluid-containing means for applying a measured fluid pressure to a cardiovascular system for measuring pressures arising in said sphygmomanometric system, said sphygmomanometric system including pressure measuring means for measuring said fluid pressure, said sphygmomanometric system also including a regulator valve means connected to said fluid-containing means and being responsive to said pressures to bleed fluid, from said fluid-containing means and to the external atmosphere, for decreasing said measured fluid pressure at a predetermined slow bleed rate;

said sphygmomanometric system further including exhaust valve means connected to said fluid-containing means for bleeding fluid, from said sphygmomanometric system, to the external atmosphere, and independently of said regulator valve means, for decreasing said measured fluid pressure at predetermined rates essentially consisting of a substantially nil rate, fast bleed rate, and a dump rate;

said exhaust valve means having control means which is manually operable for adjusting the rate of bleed of said exhaust valve means, said control means including means automatically restricting said control means to adjusting the last said rates of bleed solely and selectively to nil, fast bleed and dump.

2. The sphygmomanometric system of claim 1 comprising a housing having a fitting interconnecting said fluid containing means with the external atmosphere, there being a bleed passage in said fitting through which said fluid is to be bled to said atmosphere, and said exhaust valve means having a valve element in said housing for hindering flow through said passage in varying degrees ranging from substantially completely to substantially not at all, said valve element having connected thereto said control means for operation of said valve element such that flow through said passage can correspond only to said nil, fast bleed or dump rates.

3. The sphygmomanometric system of claim 2, said fitting having spaced flange means projecting therefrom along and across a predetermined path, and said control means having flange means projecting therefrom across said path, said control means being movable along said path for causing its said flange means to contact said spaced flange means, as well as for operating said valve element, said spaced flange means preventing such motion of said control means unless said spaced flanged means are contacted by said control means' flange means with enough force to cause a contacted flange means to give way.

4. The sphymomanometric system of claim 3, wherein said flange means of said control means is elastically supported so as to constitute said flange means which give way when contacting said spaced flange means.

5. The sphygmomanometric system of claim 4, wherein there is pump means connected to said fluid-containing means for providing said fluid-containing means with the fluid whose pressure is applied by said fluid-containing means to said cardiovascular system.

6. The sphygmomanometric system of claim 3, wherein there is pump means connected to said fluid-containing means for providing said fluid-containing means with the fluid wose pressure is applied by said fluid-containing means to said cardiovascular system.

7. The sphygmomanometric system of claim 2, wherein there is pump means connected to said fluid-containing means for providing said fluid-containing means with the fluid whose pressure is applied by said fluid-containing means to said cardiovascular system.

8. The sphygmomanometric system of claim 1, wherein there is pump means connected to said fluid-containing means for providing said fluid-containing means with the fluid whose pressure is applied by said fluid-containing means to said cardiovascular system.

* * * * *